United States Patent
Yamaguchi

(10) Patent No.: US 7,534,581 B2
(45) Date of Patent: May 19, 2009

(54) METHOD FOR MEASUREMENT OF ACTIVITY OF HOMOCYSTEINETHIOLACTONE HYDROLYZING ENZYME

(75) Inventor: Masahiro Yamaguchi, Osaka (JP)

(73) Assignee: Alfresa Pharma Corporation, Osaka-Shi (JP)

( * ) Notice: Subject to any disclaimer, the term of this patent is extended or adjusted under 35 U.S.C. 154(b) by 247 days.

(21) Appl. No.: 11/578,729

(22) PCT Filed: Apr. 12, 2005

(86) PCT No.: PCT/JP2005/007050

§ 371 (c)(1), (2), (4) Date: Oct. 18, 2006

(87) PCT Pub. No.: WO2005/103286

PCT Pub. Date: Nov. 3, 2005

(65) Prior Publication Data

US 2007/0243571 A1  Oct. 18, 2007

(30) Foreign Application Priority Data

Apr. 19, 2004 (JP) .............................. 2004-122926

(51) Int. Cl.
*C12Q 1/34* (2006.01)
(52) U.S. Cl. ........................................................ 435/18
(58) Field of Classification Search ................ None
See application file for complete search history.

(56) References Cited

OTHER PUBLICATIONS

Kosaka, T. et al. Investigation of the Relationship Between Atherosclerosis and Paraoxonase . . . Clinica Chimica Acta 359(1-2)156-162, 2005.*

Togawa T. et al. Measurement of Homocysteine Thiolactone Hydrolase Activity . . . J of Chromatography B 819(1)67-72, May 5, 2005.*

Satch T. et al. Current Progress on Esterases. Drug Metabolism and Dispostion 30(5)488-493, 2002.*

Billecke, S. et al., "Human serum paraoxonase (PON1) isozymes Q and R hydrolyze lactones and cyclic carbonate esters," Drug Metabolism and Disposition, 2000, vol. 28 No. 11, pp. 1335-1342, The American Society for Pharmacology and Experimental Therapeutics.

Jakubowski, Hieronim, "Calcium-dependent human serum homocysteine thiolactone hydrolase: a protective mechanism against protein *n*-homocysteinylation," The Journal of Biological Chemistry, Feb. 11, 2000, vol. 275 No. 6, pp. 3957-3962, The American Society for Biochemistry and Molecular Biology, Inc.

Draganov, Dragomir I. et al., "Rabbit serum paraoxonase (PON3) is a high density lipoprotein-associated lactonase and protects low density lipoprotein against oxidation," The Journal of Biological Chemistry, Oct. 27, 2000, vol. 275 No. 43, pp. 33435-33442, The American Society for Biochemistry and Molecular Biology, Inc.

Sorenson, R.C. et al., "Reconsideration of the catalytic center and mechanism of mammalian paraoxonase/arylesterase," Proceedings of the National Academy of Science of the United States of America, Aug. 1995, vol. 92, pp. 7187-7191.

* cited by examiner

*Primary Examiner*—Ralph Gitomer
(74) *Attorney, Agent, or Firm*—Millen, White, Zelano, Branigan, P.C.

(57) ABSTRACT

The present invention provides a method for the measurement of the activity of homocysteinethiolactone hydrolyzing enzyme in a sample. The method involves mixing and reacting γ-thiobutyrolactone and the sample in the presence of a cholinesterase inhibitor, and measuring 4-mercaptobutyric acid product. The method is safe and easy to operate, since it does not involve the use of a radioactive substrate, and is free of influence of other compounds contained in a bodily sample.

13 Claims, 4 Drawing Sheets

METHOD FOR MEASUREMENT OF ACTIVITY OF HOMOCYSTEINETHIOLACTONE HYDROLYZING ENZYME

TECHNICAL FIELD

The present invention relates to a method for measurement of the activity of the homocysteinethiolactone hydrolyzing enzyme, a reagent for measurement of the activity of the homocysteinethiolactone hydrolyzing enzyme, and a kit utilizing the reagent for measurement of the activity of the homocysteinethiolactone hydrolyzing enzyme.

BACKGROUND ART

Homocysteinemia is known to be one of risk factors of the development of myocardial infarction and arteriosclerosis. Precise mechanisms involved in it, however, have not yet been clarified, though such different hypotheses are proposed that are based on oxidation stress of homocysteine, impaired functioning of nitrogen oxide (NO), the endoplasmic reticulum put under stress, etc. Among these is the homocysteinethiolactone (hereinafter referred to as "HTL") based hypothesis.

DISCLOSURE OF INVENTION

In the process of protein synthesis, certain aminoacyl-tRNAs are known to erroneously take up homocysteine instead of other amino acids. Although homocysteine thus taken up will not be incorporated into the protein being newly synthesized, cyclic HTL is formed in a process to correct this error. HTL freely passes through the cell membrane under a physiological condition and thus diffuses out of the cell. Chemically, HTL is rather active and acylates amino groups in proteins. In fact, it has been reported that HTL deactivates lysine oxidizing enzymes and modifies apoprotein B in the LDL, and some researcher think that HTL is the very culprit of the cell toxicity observed with homocysteine. On the other hand, since HTL, when added to the serum, is converted to homocysteine in a short time, it has been thought that a HTL hydrolyzing enzyme is present in the serum, protecting the body through decomposition of HTL.

Jakubowski and his colleagues, having purified a HTL hydrolyzing enzyme from the HDL fraction of human serum and determined its N-terminal sequence, confirmed that it is identical to a known enzyme called paraoxonase (hereinafter referred to as "PON"). Based on this and also on the fact that HTL hydrolyzing activity was not detected in the serum from PON-deficient mice, the HTL hydrolyzing enzyme was confirmed to be identical to PON (see Non-patent Document 1).

The mechanism of action of PON, a calcium-dependent enzyme, is not fully elucidated. This enzyme was first found as an enzyme that hydrolyses paraoxon, a metabolite of parathion, a pesticide. This enzyme, however, hydrolyses other substrates such as phenyl acetate, too. Though its physiological substrate is unknown, PON is thought to act in the direction to protecting serum lipoproteins from their oxidative degradation. In fact, since it was found that PON is a component of the HDL and hydrolyzes oxidized phospholipids and cholesterol hydroperoxide, attention has been drawn to the relation between this enzyme and arteriosclerotic diseases. PON gene been shown to consist of at least three relating genes, PON1, PON2 and PON3. In species including human and some other animals (mice, dogs and birds), sequences encoding PON2s have been found, which are apparently unable to hydrolyze paraoxon. In human, a sequence also occurs which encodes PON3. Though, according to some reports of epidemiological studies on Gln/Arg polymorphism at position 192 of PON1, the arginine-type, which has higher enzyme activity, occurs more frequently in patients of cardiac infarction, it remains unknown whether there is any relation between PON gene polymorphism and arteriosclerotic diseases, since there are many other reports that deny the presence of such a relation.

Even though PON and the HTL hydrolyzing enzyme, as mentioned above, is one and identical enzyme, no proper assessment of the enzyme in the body has been made so far. That is, it is unlikely that paraoxon, the substrate used in the measurement of PON activity, is the physiological substrate for the enzyme. Further, if there exists a PON2 that apparently is incapable of hydrolyzing paraoxon or a PON3 whose properties are not well known, there then would be a possibility that measurement of PON activity, which relies on paraoxon as the substrate, cannot serve as an accurate method of assessment. Recently, PON3 was purified from rabbit serum. Rabbit PON3 was found to be a protein having a molecular weight 40-KDa contained in the HDL fraction of the serum. In contrast to PON1, PON3 has no paraoxon hydrolyzing activity, but hydrolyses lactones. And it has also been reported to function more protectively against LDL oxidation (see Non-patent Document 2). Further, it has been reported that PON1 also hydrolyzes various lactones (Non-patent Document 3). Thus, in the measurement of the enzyme, it is thought that employment of HTL, which is seemed to be a more physiological substrate, instead of the non-physiological substrate paraoxon, will lead to clarification of the precise role of the enzyme in the body and further to the possibility of revelation of the relations between the enzyme and arteriosclerotic diseases.

Measurement of HTL hydrolyzing activity has so far been performed using HTL labeled with a radioisotope, $[^{35}S]$. However, this method of measurement entails difficult problems that prevent it from becoming a commonly used testing method, since it is subject to certain restrictions on operators and facilities in its practice, raises problems of safety and on how to dispose of the radioactive reagents, and, further, requires complicated processes such as thin layer chromatography to separate the reaction product, i.e., homocysteine, from undecomposed HTL.

A method based on HPLC was recently developed. This method, however, also entails difficult problems that prevent it from becoming a commonly used testing method, for it requires much time for conducting even a single test.

There also is reported another method which does note rely on a radioactive isotope and in which the activity of HTL hydrolyzing enzyme is measured by determining homocysteine produced by reacting PON on HTL employed as a substrate (see Non-patent Document 3). In more detail, in this reported method, the thiol group of homocysteine produced from HTL by PON is subjected to substitution reaction with DTNB (5,5'-dithiobis(2-nitrobenzoic acid)) to release 2-nitro-mercaptobenzoic acid, whose yellow color then is traced. However, this is a report based on using a purified enzyme, and no attention is paid in it to any influence of human serum or components of bodily fluid.

On the other hand, human serum PON1 is known to hydrolyzes a number of lactones and thiolactones including paraoxon, phenyl acetate, 2-coumarone, dihydrocoumarin, homogentisic acid lactone, γ-butyrolactone and derivatives thereof, α-angelicolactone, oxabicyclooctenones, β-hydroxybutyrolactone, δ-lactones such as δ-valerolactone, ε-caprolactone, γ-thiobutyrolactone, homocysteinethiolactone, N-acetylhomocysteinethiolactone, propylene carbonate, 4-(1-propenyloxymethyl) -1,3-dioxolan-2-one, and the like (see above-cited Non-patent Document 3).

[Non-patent document 1] The Journal of Biological Chemistry Vol. 275, No. 6, 3957-3962, 2000

[Non-patent Document 2] The Journal of Biological Chemistry Vol. 275, No. 43, 33435-33442, 2000

[Non-patent Document 3] Drug Metabolism and Disposition Vol. 28, No. 11, 1335-1342, 2000

DISCLOSURE OF INVENTION

Problems to be Solved by the Invention

Against the above-mentioned background, the objective of the present invention is to provide, in the field of measurement of HTL hydrolyzing enzyme activity, a method for the measurement that does not use a radioactive substrate, and is safe, easy to operate, and unsusceptible to other compounds occurring in a sample from the body.

In the study addressed to the above objective, the present inventor found that, as described later in the section of the examples, hydrolysis of HTL in samples from the body, such as serum or plasma, is influenced by their ingredients, among others, serum albumin, and that a method for measurement relying on HTL as the substrate can hardly become a general testing method applicable to human serum or bodily fluid. Though there are a number of reports on the esterase activity of albumin, there also is a negative report that attributes the alleged effect of albumin in the measurement of cholinesterase activity to contaminant cholinesterase contained in commercially available albumin products (Pharmaceutical Research Vol. 18, No. 10, 1435-1439). Investigation made with reference to this report confirmed that the effect of albumin in the measurement of HTL hydrolysis activation is not due to contaminant cholinesterase but due to an esterase-like activity of albumin. There are many reports showing that the esterase-like activity of albumin is inhibited by addition of free fatty acids, surfactants, and the like, but the effect of those compounds varies depending on a given enzyme or substrate to be measured. Therefore they are not highly specific inhibitors to the esterase-like activity of albumin. Thus, trying to attain specific inhibition of the esterase-like activity of albumin would require much time and efforts in search of an inhibitor.

HTL rapidly undergoes autolysis in near neutral solutions. Therefore, there has been a problem, in HTL-based measurement of the activity of the HTL hydrolyzing enzyme, that it gives high reagent-blank values and thus could affect the accuracy of measurement and stability of the solution used in it.

Means to Solve the Problem

The present inventor, as a result of studies to solve the above-mentioned problems involved in the measurement of the activity of the homocysteinethiolactone hydrolyzing enzyme contained in samples from the body such as serum and the like, found that the problems are solved by employing γ-thiobutyrolactone (hereinafter referred to as "TBL") as the substrate in the measurement of activity of the HTL hydrolyzing enzyme. Briefly, the present inventor found the following advantages of the method for measurement of the activity of the HTL hydrolyzing enzyme using TBL as the substrate: that it is not affected by the presence of albumin (see the section of Examples); that the substrate is stable and thus gives lowered reagent-blank values (see the section of Examples); that its working solution is stored for an extended period of time; and that as it has no optical isomer, TBL exhibits steady specificity and is available at low cost.

However, it was also found at the same time that, in the measurement of the activity of the HTL hydrolyzing enzyme, employment of TBL, instead of HTL, as the substrate makes the measurement susceptible to cholinesterase, i.e., cholinesterase hydrolyzes TBL (see the section of Examples). Furthermore, through studies using several cholinesterase inhibitors to avoid the influence of cholinesterase, the present inventor found that those cholinesterase inhibitors act specifically on cholinesterase and do not affect HTL hydrolyzing enzymes (see the section of Examples). In addition, it was also found that, under the presence of a cholinesterase inhibitor, a strong correlation is present between measured activities of HTL hydrolyzing enzymes using TBL as the substrate and measured activities of HTL hydrolyzing enzyme using HTL as the substrate, in their Ca-dependency. Thus, it was found that the method of measurement of the activity of the HTL hydrolyzing enzyme using TBL as the substrate is highly specific method for the measurement of the activity of the HTL hydrolyzing enzyme.

Thus, the present inventor completed the present invention upon the finding that the activity of the HTL hydrolyzing enzyme can be measured with increased accuracy and specificity, without using a radioactive substrate, and more safely and with ease, and free of the influence of other compounds occurring in the body (albumin) by conducting a reaction using TBL as the substrate in the presence of a cholinesterase inhibitor.

Thus, the present invention provides a method for measurement of the activity of the homocysteinethiolactone hydrolyzing enzyme in a sample comprising mixing and reacting γ-thiobutyrolactone and the sample in the presence of a cholinesterase inhibitor, and measuring 4-mercaptobutyric acid thereby produced.

The present invention further provides the method for measurement as mentioned above, wherein the reaction is conducted in the presence of a divalent cation. As a divalent cation, $Ca^{2+}$, $Ni^{2+}$ and $Fe^{2+}$, for example, may be employed at a concentration of, e.g., 0.1-10 mM.

In the above-mentioned method for measurement, physostigmine or salts thereof, neostigmine or salts thereof, and 4-bromobenzeneboronic acid or salts thereof and the like may be used as a cholinesterase inhibitor. Hereupon, physostigmine or salts thereof may be used at a concentration of, e.g., 10 μM to 10 mM, neostigmine or salts thereof, e.g., 10 μM to 10 mM, and 4-bromobenzeneboronic acid or salts thereof, e.g., 10 μM to 1 mM.

The present invention further provides the method for measurement as mentioned above, wherein the produced 4-mercaptobutyric acid is measured using a thiol group detection reagent. Hereupon, as a thiol group detection reagent, 5,5'-dithiobis(2-nitrobenzoic acid), 4,4'-bis(dimethylamino)benzhidrol, 2,2'-dithio-dipyridine, 4,4'-dithiodipyridine, 2,2'-dithiobis(5-nitropyridine) or 6,6'-dithiobis-nicotinic acid, for example, may be used.

The present invention further provides a reagent for measurement of the activity of the homocysteinethiolactone hydrolyzing enzyme comprising γ-thio-butyrolactone and a cholinesterase inhibitor.

In the above-mentioned reagent, as a cholinesterase inhibitor, physostigmine or salts thereof, neostigmine or salts thereof, 4-bromobenzeneboronic acid or salt thereof, for example may be used. The reagent may further comprise a thiol group detection reagent. As thiol group detection reagents, 5,5'-dithiobis(2-nitrobenzoic acid), 4,4'-bis(dimethylamino)benzhidrol, 2,2'-dithiodipyridine, 4,4'-dithiodipyridine, 2,2'-dithiobis(5-nitropyridine) or 6,6'-dithiobisnicotinic acid, for example, may be used.

The present invention further provides a kit for measurement of the activity of the homocysteinethiolactone hydrolyzing enzyme. Such a kit may comprise, e.g., containers separately containing γ-thiobutyrolactone and a cholinesterase inhibitor, or further comprise an additional container separately containing a thiol group detection reagent. Or it may comprise multiple containers or one container having multiple separated zones, containing a mixture consisting of γ-thiobutyrolactone and a cholinesterase inhibitor or further of a thiol group detection reagent, or comprise strips of paper impregnated with γ-thiobutyrolactone and a cholinesterase inhibitor or further with a thiol group detection reagent.

Effect of the Invention

The present invention as defined above provides a means for measurement of the activity of the homocysteinethiolactone hydrolyzing enzyme, which means is safe, quick, highly specific and convenient to use in daily examinations, without using a radioactive substrate. Furthermore, the present invention is particularly useful in the measurement of the activity of the homocysteinethiolactone hydrolyzing enzyme in samples taken from the body, such as the blood, serum, plasma and the like, and thereby makes it easy to give diagnosis of, and comprehend the progression of, diseases resulting from alterations of HTL hydrolyzing enzyme activity.

Figure 1:
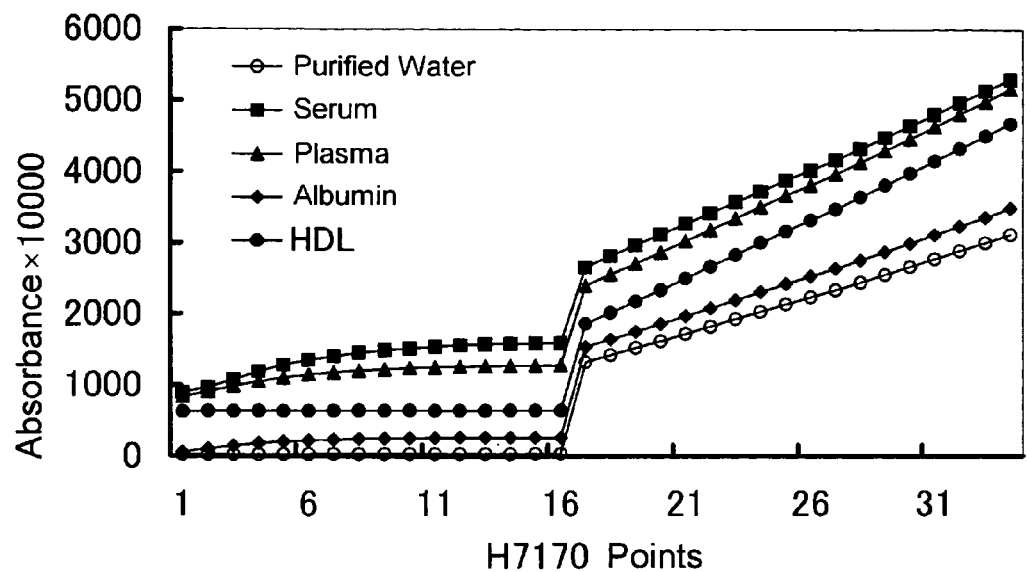
FIG. 1 illustrates the time profiles taken of the measurement of the activity of the HTL hydrolyzing enzyme in samples using Reagent 1(A).

BEST MODE FOR CARYING OUT THE INVENTION (Characteristics of the Method of the Present Invention)

The first characteristic of the method for the measurement of the activity of the HTL hydrolyzing enzyme consists in that it utilizes TBL, in place of HTL, as a substrate, which is reacted with a HTL hydrolyzing enzyme-containing sample, and 4-mercaptobutyric acid thus formed through decomposition by the HTL hydrolyzing enzyme is measured to determine the activity of the HTL hydrolyzing enzyme. The second characteristic of the present invention consists in that the reaction of TBL with HTL hydrolyzing enzyme in a sample is conducted in the presence of a cholinesterase inhibitor. And the third characteristic of the present invention consists in that it measures 4-mercaptobutyric acid produced by the reaction, based on the change in the color development by reacting it with a SH detection reagent. According to the present invention, the measurement can be performed safely, quickly, specifically and conveniently, for it does no use a radioactive substrate.

Description will be given below to the reagent for measurement of the activity of the HLT hydrolyzing enzyme, a method for measurement using the reagent, and a kit for measurement of the activity of the HLT hydrolyzing enzyme, in the order.

(Reagent for the Activity of the HTL Hydrolyzing Enzyme)

The reagent for measurement of the activity of the HTL hydrolyzing enzyme of the present invention comprises a substrate for HTL hydrolyzing enzyme. As a substrate, TBL is employed. In general, the substrate is provided in the form of a liquid. The substrate is provided at a concentration that allows its final concentration in the reaction solution to fall within the range of 5-100 mM, more preferably 10-50 mM.

The reagent for measurement of the activity of the HTL hydrolyzing enzyme is preferably provided in the form of a liquid. The pH of a reaction solution of HTL hydrolyzing enzyme is about 6-9, preferably 7-8, and the reagent for measurement of the activity of the HTL hydrolyzing enzyme may contain, if needed, a buffering agent to make the pH of the reaction solution fall within the region, in accordance with the nature of the sample to be analyzed.

In the reagent of the present invention for measurement of the activity of the HTL hydrolyzing enzyme, the substrate for HTL hydrolyzing enzyme may be dissolved in water or a buffer of pH 2-9 (e.g., HEPES buffer, citrate buffer, tartrate buffer, acetate buffer, Tris buffer, borate buffer, MOPS buffer, PIPES buffer, Good's buffer, etc.).

In the reagent of the present invention for measurement of the activity of the HTL hydrolyzing enzyme, a SH detection reagent may be dissolved in a buffer of pH 2-9 (e.g., HEPES buffer, citrate buffer, tartrate buffer, acetate buffer, Tris buffer, borate buffer, MOPS buffer, PIPES buffer, Good's buffer, etc.). Preferable pH is 6-8.

In the reagent of the present invention for measurement of the activity of the HTL hydrolyzing enzyme, a SH detection reagent may be any one of the compounds, without specific limitation, insofar as it, after reacting with a SH group, quantitatively exhibits color changes (in the visible or ultraviolet range). Examples include DTNB (5,5'-dithiobis(2-nitrobenzoic acid)), 4,4'-bis(dimethylamino)benzhidrol, 2,2'-dithiodipyridine, 4,4'-dithiodipyridine, 2,2'-dithiobis(5-nitropyridine) or 6,6'-dithiobisnicotinic acid, for example, may be used. A SH detection reagent may be used at its final concentration falling within the range of 0.1-10 mM, more preferably 0.5-2 mM in the reaction solution.

In the reagent of the present invention for measurement of the activity of the HTL hydrolyzing enzyme, a cholinesterase inhibiter may be any one of the compounds which specifically inhibit cholinesterase, and such cholinesterase inhibitors may be used as physostigmine and salts thereof (e.g., physostigmine sulfate), neostigmine or salts thereof (e.g., neostigmine bromide), 4-bromobenzeneboronic acid or salts thereof, tetraethyl pyrophosphate, tri-o-cresyl phosphate, octamethylpyrophosphohole tetramide, tetramonoisopropylphosphole tetramide, phosphorin and salts thereof (e.g., phosphorin iodide), edrophonium and salts thereof (e.g. edrophonium bromide), ethopropazine and salts thereof (e.g., ethopropazine hydrochloride), fluostigmine, tetrazoline and salts thereof (e.g., tetrazoline hydrochloride), tetrazolone and salts thereof (e.g., tetrazolone hydrochloride), gramine, desoxypeganine and salts thereof (desoxypeganine hydrochloride) and the like. Preferably used are physostigmine and salts thereof, neostigmine and salts thereof, and 4-bromobenzeneboronic acid and salts thereof A choline esterase in use may be set at any concentration as desired, insofar as it, at the concentration, effectively inhibits cholinesterase in a given sample. In the case of physostigmine or its salt, or neostigmine bromide or its salt, they may be used at, e.g., 10 µM to 10 mM, and more preferably 20 µM to 5 mM. In the case of 4-bromobenzeneboronic or salts thereof, they may be used at, e.g., 10 µM to 1 mM, more preferably at 20 µM to 100 µM.

As the activity of HTL hydrolyzing enzyme is known to be enhanced in the presence of divalent cations such as $Ni^{2+}$, $Fe^{2+}$, $Ca^{2+}$ etc. (aforementioned Non-patent Document 1), it is preferable that the reagent of the present invention for measurement of the activity of the HTL hydrolyzing enzyme simultaneously contains a divalent cation. Examples of divalent cations include $Ni^{2+}$, $Fe^{2+}$, $Ca^{2+}$ etc., among which $Ca^{2+}$ is particularly preferred. A divalent cation may be used at its final concentration falling within the range of 0.1-10 mM, more preferably 0.5-5 mM in the reaction solution.

The reagent of the present invention for measurement of the activity of the HTL hydrolyzing enzyme may contain a surfactant. Examples of surfactants that may be used include, but not limited to, anionic surfactants, nonionic surfactants, bile salts and derivatives of bile salts, etc. It is possible to use a single type of surfactant or to use two or more types of surfactants in combination. Further, it is also possible to use two or more surfactants of the same type.

In the method for measurement of the present invention, an anionic surfactant is preferably at least one compound selected from fatty acid salts (e.g., sodium stearate, potassium oleate, etc.), sulfuric acid alkyl ester salts (e.g., sodium lauryl sulfate, lithium lauryl sulfate, etc.), benzenesulfonic acid alkyl ester salts (e.g., sodium lauryl benzenesulfonate, sodium 4-n-octyl benzenesulfonate, etc.), naphthalenesulfonic acid alkyl ester salts (e.g., sodium 2-naphthalenesulfonate), sulfosuccinic acid alkyl ester salts (e.g., sodium dialkyl sulfosuccinate), alkyl diphenylether disulfonic acid ester salts (e.g., sodium alkyl diphenyl ether disulfonate, etc.), alkyl phosphoric acid ester salts (e.g., potassium alkyl phosphate, etc.), sulfuric acid polyoxyethylene alkyl ester salts (e.g., sodium polyoxyethylene lauryl ether sulfate, triethanolamine polyoxyethylene alkyl ether sulfate, etc.), sulfuric acid polyoxyethylene aklylaryl ether salts (e.g., sodium polyoxyethylene nonylphenyl ether sulfate, etc.), alkylsulfonic acid salts (e.g., sodium octanesulfonate, sodium nonanesulfonate, sodium decanesulfonate, sodium tridecanesulfonate, etc.), naphthalenesulfonic acid formalin condensates (e.g., sodium salt of β-naphthalenesulfonic acid formalin condensate, etc.), and polyoxyethylenealkyl phosphate.

In the method for measurement of the present invention, a nonionic surfactant is at lease one compound preferably selected from polyoxyethylene alkyl ethers (e.g., polyoxyethylene lauryl ether, polyoxyethylene cetyl ether, polyoxyethylene stearyl ether, polyoxyethylene oleyl ether, etc.), polyoxyethylene alkylaryl ethers (e.g., polyoxyethylene octylphenyl ether, polyoxyethylene nonylphenyl ether, polyoxyethylene isooctylphenyl ether, etc.), polyoxyethylene derivatives (polyoxyethylene polyoxypropylene condensate, etc.), sorbitan fatty acid esters (e.g., sorbitan monolaureate, sorbitan monopalmitate, sorbitan monostearate, sorbitan monooleate, sorbitan trilaurate, sorbitan tristearate, sorbitan trioleate, sorbitan distearate, etc.), polyoxyethylenesorbitan fatty acid esters (e.g., polyoxyethylene-sorbitan monolaurate, polyoxyethylenesorbitan monopalmitate, polyoxyethylene-sorbitan monostearate, polyoxyethylenesorbitan monooleate, polyoxyethylenesorbitan tristearate, polyoxyethylenesorbitan trioleate, etc.), polyoxyethylenesorbitol fatty acid esters (e.g., polyoxyethylensorbit tetraoleate, etc.), glycerin fatty acid esters (e.g., glycerol monostearate, glycerol monooleate, etc.), polyoxyethylene fatty acid esters (e.g., polyethyleneglycol monolaurate, polyethyleneglycol monostearate, polyethylene-glycol monooleate, polyethyleneglycol distearate, etc.), polyoxyethylene alkylamine, and alkylalkanol amide.

In the method for measurement of the present invention, bile acid salts or bile acid derivatives is preferably at least one compound selected from sodium cholate, sodium deoxycholate, sodium chenodeoxycholate, sodium dehydrocholate, sodium taurocholate, sodium taurolitocholate, sodium taurodeoxycholate, sodium taurochenodeoxycholate, sodium tauroursodeoxycholate, sodium taurodehydrocholate, 3-[(3-chloramidepropyl)dimethylammonio]propanesulfonic acid (CHAPS), 3-[(3-chlor -amidepropyl)dimethylammonio]-2-hydroxypropanesulfonic acid (CHAPS O), N,N-bis -(3-D-gluconamidepropyl)cholamide (BIGCHAP), and N,N-bis(3-D-gluconamide -propyl)deoxycholamide (deoxy-BIGCHAP).

Further, the reagent of the present invention for measurement of the activity of the HTL hydrolyzing enzyme may contain, in addition to those above-mentioned, one or more compounds conventionally used in enzyme activity measurement, such as buffering agents, stabilizers, activators, diluents, preservatives, etc.

(Measurement of the Activity of the HTL Hydrolyzing Enzyme According to the Present Invention)

In the present invention, 4-mercaptobutyric acid, which is formed by hydrolysis of TBL by HTL hydrolyzing enzyme in the presence of a cholinesterase inhibitor, may be measured by any one of methods as desired, such as HPLC or the like. Among them, preferred in the present invention is a method in which 4-mercaptobutyric formed by the reaction is measured, qualitatively or quantitatively, by reacting it with a SH-group detection reagent and measuring thus caused changes in color. The concentration of a SH-group detection reagent in the reaction liquid may be set as desired at any one of concentrations conventionally employed for SH-group detection, e.g., 0.1-10 mM, or 0.5-5 mM.

A sample with which the activity of the HTL hydrolyzing enzyme is to be measured may be human or animal body fluid such as blood, serum, urine or amnion liquid, as well as human or animal cells, organs or their extract liquid and the like. A HTL hydrolyzing enzyme product and a sample such as serum to be analyzed containing the HTL hydrolyzing enzyme are subjected to the reaction for measurement after dilution as desired with a buffer of pH 6-9 (e.g., HEPES buffer, Tris buffer, phosphate buffer, borate buffer, MOPS buffer, PIPES buffer Good's buffer, etc.) and kept at 20-40° C. Sodium chloride and potassium chloride may be added to these buffers to attain a proper concentration of salts.

In the measurement of changes in color as a result of the reaction of 4-mercaptobutyric acid and a SH detection reagent, absorbance is measured at a wavelength that is suitable to the reagent employed. Measurement may be made either by an end-point method or a rate method. In the case of an end-point method, it is necessary that, for determining the activity of the HTL hydrolyzing enzyme, absorbance be subtracted that is generated as a result of color development by the reaction of the SH-group detection reagent and free SHgroups of proteins occurring in a sample, by reacting the sample with a reagent for measurement which contains other ingredients but the substrate. In the case of a rate method, measurement of absorbance may be made while the change in color development is taking place quantitatively. HTL hydrolyzing enzyme activity may be calculated on the basis of the molecular extinction coefficient of the SH group detection reagent when it develops color, or based on absorbance measured after color development using a predetermined quantity of a standard compound which has free SH groups.

Measurement of the activity of the HTL hydrolyzing enzyme according to the present invention may be carried out either by hand or on an automatic analyzer. Change in color is measured which is generated by the reaction of free SH group-carrying 4-mercaptobutyric acid formed by HTL hydrolyzing enzyme and a SH-group detection reagent. For example, when DTNB is used as a SH-group detection reagent, HTL hydrolyzing enzyme activity can be determined with a high degree of accuracy by detecting the change in absorbance at the wavelength of 400-500 nm and then calculating the change in absorbance per unit of time (so-called rate assay method).

A method for measurement is specifically described below. First, a SH-group detection solution prepared by dissolving a reagent in a suitable buffer solution (for example, 0.2 M MOPS buffer (pH 7.2) containing SH-group detection reagent, 0.1 mM physostigmine sulfate, and 5 mM $CaCl_2$) and a substrate solution are prepared. A suitable amount of human pool serum or human serum is mixed with the SH-group detection solution, and the substrate solution then is added to the mixture to react. Reaction temperature may be 20-40° C., preferably 37° C. After the addition of the substrate solution, absorbance is measured in a suitable time window (e.g., from 2-minute up to 4-minute time points), change in absorbance per unit of time calculated, and from this, based on the molecular extinction coefficient of the SH detection reagent, the activity value of the HTL hydrolyzing enzyme may be determined.

Where an automatic measurement is made based on a rate method, the aforementioned SH-group detection solution and a substrate solution are first prepared. Using, for example, a H-7170 automatic analyzer (Hitachi, Ltd.), measurement is made in accordance with parameters for the measurement. Human pool serum or human serum is mixed with the SH-group detection solution, and, after a predetermined length of time, the substrate solution is further mixed to allow the reaction to start. Change in absorbance (time profile) then is monitored, and amount of the change in absorbance per unit of time (1 min) is determined from 2-minute time point after the start of the reaction up to 4-minute time point. The activity value of HTL hydrolyzing enzyme for each sample is calculated according to the following mathematical formula, based on the change in absorbance per unit of time measured with the sample ($\Delta ES$), the change in absorbance per unit of time measured with purified water in place of the sample ($\Delta EB$), as well as the molecular extinction coefficient of the SH-group detection reagent ($\epsilon 1$) in the reaction solution and at the main wavelength for the measurement, and the molecular extinction coefficient of the SH-group detection reagent ($\epsilon 2$) at the supplementary wavelength for measurement.

$$\text{Activity } (U/L) = \frac{(\Delta ES - \Delta EB) \times \text{final reaction volume} \times 10^6}{(\epsilon 1 - \epsilon 2) \times \text{sample volume} \times \text{light path length}}$$

(Kit for Measurement of the Activity of the HTL Hydrolyzing Enzyme)

The kit of the present invention for measurement of the activity of the HTL hydrolyzing enzyme comprises the above-mentioned reagent for measurement of the activity of the HTL hydrolyzing enzyme which contains a substrate, a SH-group detection reagent, a divalent cation, a cholinesterase inhibitor, and, as needed, other additives. The kit may be provided, for example, in the form of ampoules or vials each containing TBL, a cholinesterase inhibitor, or a SH-group detection reagent, or a mixture of them, or in the form of wells in each of which a predetermined amount of the reagent for measurement of the activity of the HTL hydrolyzing enzyme is injected, or in the form comprising a container containing the reagent for measurement of the activity of the HTL hydrolyzing enzyme and wells in which the measurement is to be made. By adding a sample, e.g., serum, to the reagent for measurement of the activity of the HTL hydrolyzing enzyme included in those forms of kit, the activity of the HTL hydrolyzing enzyme is measured.

Furthermore, the kit of the present invention for the measurement of the activity of the HTL hydrolyzing enzyme may be in the form of testing strips of, e.g., filter paper impregnated with the above-mentioned reagent for measurement of the activity of the HTL hydrolyzing enzyme containing the substrate TBL, a cholinesterase inhibitor, and, as desired, a SH-group detection reagent and a divalent cation, and, as needed, other additives. In this case, testing strips may be prepared by soaking those strips in a solution of the reagent and then drying them. By dipping a testing strip in serum and the like, HTL hydrolyzing enzyme activity contained is qualitatively detected. It is also possible that a SH-group detecting reagent is provided in a separately attached container, from which it is dropped onto a testing strip in which a hydrolysis reaction has taken place. Even with these testing strips-type kits, activity can, though roughly, be determined using a color table for comparison. Therefore, the kit may contain such a table for comparison.

In addition, the kit of the present invention may be provided in such a form that a solution containing the substrate and a solution containing a SH-group detection reagent are respectively contained in separate containers and mixed when they are used. In such a case, the substrate may be provided as a solution in water, a buffer solution or in a solvent such as alcohol (methanol, ethanol, etc.) or dioxane, or, alternatively, a solution and/or solvent for dissolving the substrate may separately be provided in discrete containers. Likewise, a SH-group detection reagent may be provided as a solution in water, a buffer solution or in a solvent such as alcohol (methanol, ethanol, etc.), N,N-dimethylformamide, acetone and the like, or, alternatively, a solution and/or solvent for dissolving the SH-group detection reagent may separately be provided in separate containers. Of one of those forms may be selected as desired, considering easiness of operation, amount to be used, etc. As aforementioned, since the present invention is completed on the basis of novel finding that TBL does not serve as substrate for the esterase-like activity of albumin but do serve as a substrate for cholinesterase, that finding forms the essence of the present invention. Therefore, the inventor believes that other methods for measurement of the HTL hydrolyzing enzyme activity using as a substrate, instead of TBL, one of TBL-like compounds that does not serve as substrates for the esterase-like activity of albumin but substrates for cholinesterase, will fall within the scope of equivalents to the present invention.

EXAMPLES

The present invention will be described in further detail below with reference to working examples. However, it should be noted that the present invention is not limited by those examples.

(Preparation of Lipoprotein Fraction)

The specific gravity of about 240 ml of human plasma (heparinized plasma) were adjusted to d=1.063 with KBr, and centrifuged to give a fraction containing chylomicron, VLDL and LDL. The specific gravity of the remaining fraction, about 200 ml in volume, was adjusted to d=1.21 with KBr, and centrifuged to give a fraction containing HDL. The fraction containing chylomicron, VLDL and LDL and the fraction containing HDL, and human plasma (heparinized plasma) were dialyzed against 0.1 M HEPES buffer containing 0.1 mM $CaCl_2$ (pH 7.6) and was made samples.

(Preparation of Human Albumin Solution)

Human albumin (A-1887, Sigma), human albumin (A-3782, Sigma), human albumin (05418, Fluca), human albumin (126654, Calbiochem), human albumin (A-1653, Sigma) were dissolved in purified water to prepare 5% human albumin solutions (hereinafter referred to as "HSA").

(Preparation of Human Cholinesterase Solution)

Human butyrylcholinesterase (348643, Boehringer) was dissolved in purified water to prepare a 2.0 U/ml solution.

(Preparation of Serum)

Lipidserum II (Eiken Chemical Co., Ltd) was dissolved in 3 ml of purified water.

Determiner Standard HDL-C.LDL-C for measurement (Kyowa Medex Co., Ltd.) was dissolved in 1 ml of purified water.

Five ml of human serum was collected using Veneject II vacuum blood sampling tube, plain (Terumo Corporation).

Example 1

Measurement of Hydrolyzing Enzyme Activity for HTL

Hydrolyzing enzyme activity for HTL was measured with purified water and above-mentioned samples.

Following solutions were prepared:

Reagent 1(A): SH-group detection solution; 0.2 M MOPS buffer containing 0.5 mM $CaCl_2$ and 1.0 mM DTNB (pH 7.8).

Reagent 1(B): SH-group detection solution; 0.2 M MOPS buffer containing 2 mM EDTA and 1.0 mM DTNB (pH 7.8).

Reagent 1(C): SH-group detection solution; 0.2 M MOPS buffer containing 0.5 mM $CaCl_2$, 0.1 mM physostigmine sulfate and 1.0 mM DTNB (pH 7.8).

Reagent 1(D): SH-group detection solution; 0.2 M MOPS buffer containing 0.5 mM $CaCl_2$, 0.1 mM neostigmine bromide and 1.0 mM DTNB (pH 7.8).

Reagent 2: substrate solution; aqueous solution containing 125 mM DL-HTL (Tokyo Chemical Industry Co., Ltd).

For measurement of HTL hydrolyzing enzyme activity, H-7170 automatic analyzer (Hitachi, Ltd.) was used. Parameters for measurement were as follows.

TABLE 1

| Input Items | Input |
|---|---|
| RATE-A | 21-28 POINT |
| S VOLUME | 15 ul |
| R1VOLUME | 200 ul |
| R2VOLUME | 50 ul |
| WAVELENGTH | 546-480 nm |
| K-FACTOR | 7267 |

Figure 2:
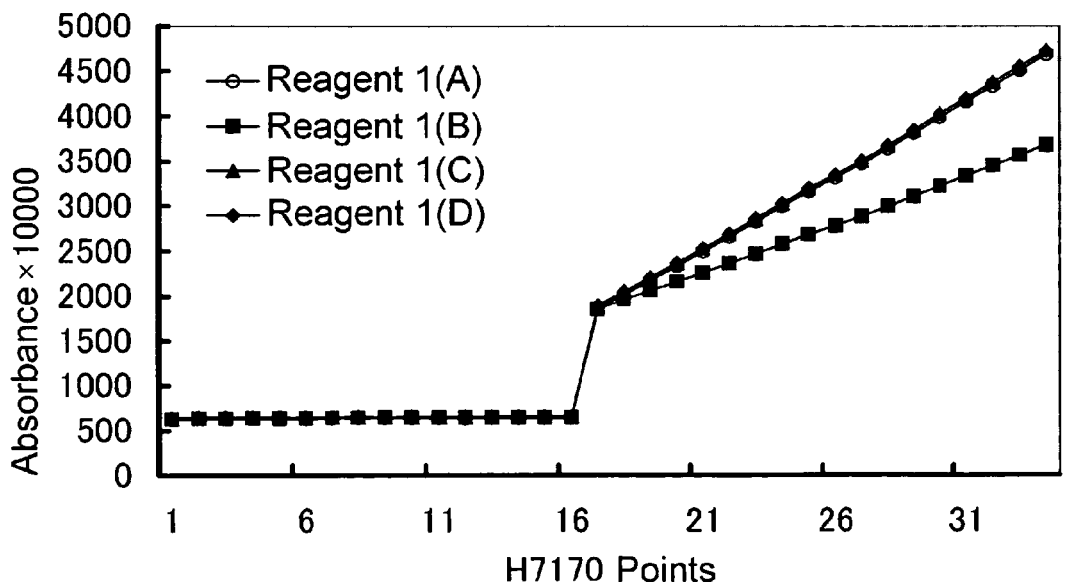
FIG. 2 illustrates the time profiles taken of the measurement of the activity of the HTL hydrolyzing enzyme in a HDL fraction using Reagents 1(A), 1(B), 1(C) or 1(D).

Following the above parameters, purified water, 15 μl of a sample and 200 μl of reagent 1(A) or 1(B) or 1(C) or 1(D) was dispensed and mixed, and, after a certain length of time at a constant temperature (37° C., 5 min), 50 μl of reagent 2 was added and mixed to allow reaction to start. The change in absorbance (time profile) is shown in FIG. 1 and FIG. 2. When reagent 2 was added to the mixture of the fraction containing serum, plasma, albumin or HDL and reagent 1(A), 1(C) or 1(D), increase in absorbance was detected which was due to the reaction of the SH-group detection reagent with DL-homocysteine, which has a free SH group, formed by hydrolysis of HTL.

As evident from FIG. 2, increase in absorbance is suppressed when calcium ion is blocked by EDTA. This indicates that the enzyme is calcium dependent for HTL hydrolyzing reaction. With reagent-blank, in which purified water was used as a sample, increase in absorbance was observed with the lapse of time after the addition of the substrate. This indicates that the substrate HTL undergoes rapid autolysis, i.e., the substrate HTL is unstable in the reaction solution.

The activity value of HTL hydrolyzing enzyme in each sample was calculated based on: the change in absorbance per unit of time (1 min) ($\Delta E$) from 2-minute up to 4-minute time points after the addition of the substrate (reagent 2), the molecular extinction coefficient of 5-thio-2-nitrobenzoic acid at the wavelength of 480 nm, $\epsilon=2509$, and the molecular extinction coefficient of the compound at the wavelength of 546 nm, $\epsilon=78$.

TABLE 2

| | Inhibitors | | | |
|---|---|---|---|---|
| Samples | No addition | EDTA.2Na | Physostigmine sulfate | Neostigmine bromide |
| HSA A-1887 | 28 | 25 | 26 | 27 |
| HSA A-3782 | 26 | 23 | 28 | 28 |
| HSA 05418 | 31 | 30 | 28 | 31 |
| HSA 126654 | 19 | 17 | 17 | 21 |
| HSA A-1653 | 26 | 22 | 25 | 20 |
| Human plasma | 141 | 36 | 138 | 139 |
| LDL | 14 | 12 | 14 | 13 |
| HDL | 156 | 6 | 156 | 154 |
| Cholinesterase | 8 | 6 | −1 | −2 |
| Lipidserum II | 178 | 100 | 172 | 178 |
| HDL-C Standard | 350 | 166 | 346 | 350 |
| Human serum | 123 | 39 | 117 | 117 |

HTL hydrolyzing enzyme activity was found localized in the HDL fraction. And, it was confirmed that, the activity of the HTL hydrolyzing enzyme does not undergo modification in the presence of a cholinesterase inhibitor, and that HTL is not hydrolyzed by purified human cholinesterase. Further, the hydrolyzing activity exhibited by HSA for the substrate HTL was found to be calcium-independent. Therefore, the hydrolyzing activity is considered to be attributable to HSA itself.

Example 2

Measurement of the activity of the Hydrolyzing Enzyme for TBL

Hydrolyzing enzyme activity for TBL was measured with above-mentioned samples and unprepared serum.

Following solutions were prepared:

Reagent 1(A): SH-group detection solution; 0.2 M MOPS buffer containing 0.5 mM $CaCl_2$ and 1.0 mM DTNB (pH 7.2).

Reagent 1(B): SH-group detection solution; 0.2 M MOPS buffer containing 2 mM EDTA and 1.0 mM DTNB (pH 7.2).

Reagent 1(C): SH-group detection solution; 0.2 M MOPS buffer containing 0.5 mM $CaCl_2$, 0.1 mM physostigmine sulfate and 1.0 mM DTNB (pH 7.2).

Reagent 1(D): SH-group detection solution; 0.2 M MOPS buffer containing 0.5 mM $CaCl_2$, 0.1 mM neostigmine bromide and 1.0 mM DTNB (pH 7.2).

Reagent 2: substrate solution; aqueous solution containing 125 mM TBL (Aldrich).

For measurement of hydrolyzing enzyme activity TBL, H-7170 automatic analyzer (Hitachi, Ltd.) was used. Parameters for measurement were as follows.

TABLE 3

| Input Items | Input |
| --- | --- |
| RATE-A | 21-28 POINT |
| S VOLUME | 15 ul |
| R1VOLUME | 200 ul |
| R2VOLUME | 50 ul |
| WAVELENGTH | 546-480 nm |
| K-FACTOR | 7267 |

Figure 3:
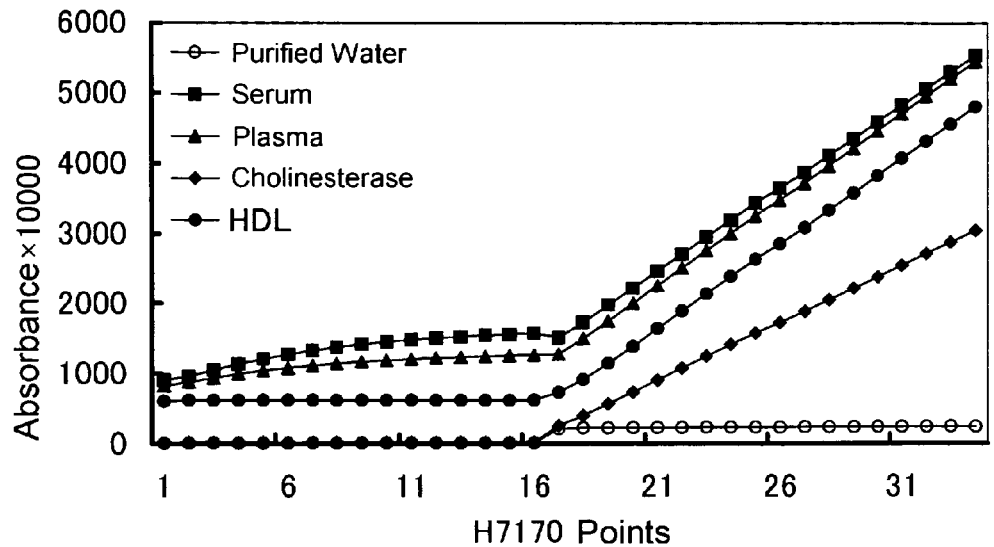
FIG. 3 illustrates the time profiles taken of the measurement of TBL hydrolyzing enzyme activity in samples using Reagent 1(A).
Figure 4:
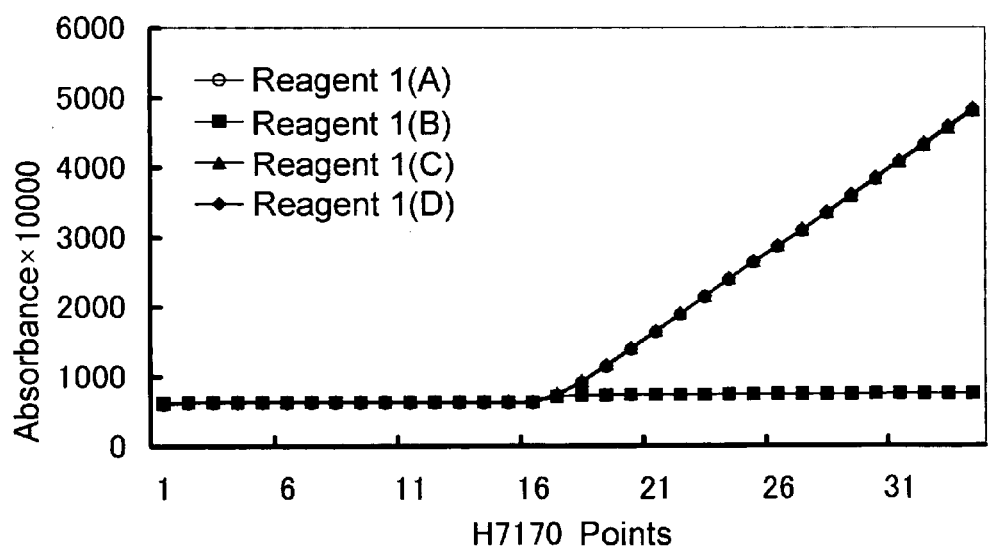
FIG. 4 illustrates the time profiles taken of the measurement of TBL hydrolyzing enzyme activity in a HDL fraction using Reagents 1(A), 1(B), 1(C) or 1(D).

Following the above parameters, 15 μl of a sample and 200 μl of reagent 1(A) or 1(B) or 1(C) or 1(D) was dispensed and mixed, and, after a certain length of time at a constant temperature (37° C., 5 min), 50 μl of reagent 2 was added and mixed to allow reaction to start. The change in absorbance (time profile) is shown in FIG. 3 and FIG. 4. When reagent 2 was added to the mixture of the fraction containing serum, plasma, cholinesterase or HDL and reagent 1(A), increase in absorbance was detected which was due to the reaction of the SH-group detection reagent with 4-mercaptobutyric acid, which has a free SH group, formed by of HTL hydrolyzing enzyme.

As evident from FIG. 4, increase in absorbance is suppressed when calcium ion is not present. This suggests that the enzyme is calcium dependent for TBL hydrolyzing reaction. As for the reagent-blank, in which purified water was used as a sample, hardly any increase in absorbance was observed after the addition of the substrate. This indicates that the autolysis of substrate TBL is slow, i.e., the substrate TBL is stable in the reaction solution.

The activity value of HTL hydrolyzing enzyme for TBL in each sample was calculated based on: the change in absorbance per unit of time (1 min) (ΔE) from 2-minute up to 4-minute time points after the addition of the substrate (reagent 2), the molecular extinction coefficient of 5-thio-2-nitrobenzoic acid at the wavelength of 480 nm, $\epsilon$=2509, and the molecular extinction coefficient of the compound at the wavelength of 546 nm, $\epsilon$=78.

TABLE 4

| | Inhibitors | | | |
| --- | --- | --- | --- | --- |
| Samples | No addition | EDTA.2Na | Physostigmine sulfate | Neostigmine bromide |
| HSA A-1887 | 7 | 8 | 4 | 5 |
| HSA A-3782 | 2 | 2 | 2 | 2 |
| HSA 05418 | 8 | 8 | 6 | 7 |
| HSA 126654 | 1 | 1 | 0 | 1 |
| HSA A-1653 | 32 | 29 | 2 | 2 |
| Human plasma | 607 | 141 | 477 | 477 |
| LDL | 21 | 3 | 21 | 22 |
| HDL | 603 | −1 | 602 | 605 |
| Cholinesterase | 403 | 399 | 1 | 2 |
| Lipidserum II | 529 | 163 | 369 | 369 |
| HDL-C Standard | 1169 | 241 | 951 | 951 |
| Human serum | 588 | 217 | 376 | 380 |

HTL hydrolyzing enzyme activity for TBL was found localized in the HDL fraction. And, it was confirmed that TBL serves as a substrate for cholinesterase, for the hydrolyzing enzyme activity for TBL is greatly altered in the presence of a cholinesterase inhibitor, and purified human cholinesterase exhibits hydrolyzing enzyme activity for TBL. Of five different HSAs, hydrolyzing enzyme activity for TBL was observed only with A-1653. As the hydrolyzing enzyme activity for TBL with A-1653 was eliminated by a cholinesterase inhibitor, it was considered due to contamination with cholinesterase.

Example 3

Measurement of Cholinesterase Activity

Cholinesterase activity was measured with the above-mentioned samples and unprepared serum. Measurement of cholinesterase activity was carried out using Nescoat ChE V-2 (Alfresa Pharma Coporation) according to the package insert.

TABLE 5

| Samples | |
| --- | --- |
| HSA A-1887 | 88 |
| HSA A-3782 | 27 |
| HSA 05418 | 23 |
| HSA 126654 | 59 |
| HSA A-1653 | 2587 |
| Human plasma | 5893 |
| LDL | 4 |
| HDL | 7 |
| Cholinesterase | 15392 |
| Lipidserum II | 7082 |
| HDL-C Standard | 9020 |
| Human serum | 8719 |

Cholinesterase activity was observed in human plasma, human cholinesterase, human serum, and HSA A-1653.

Figure 5:
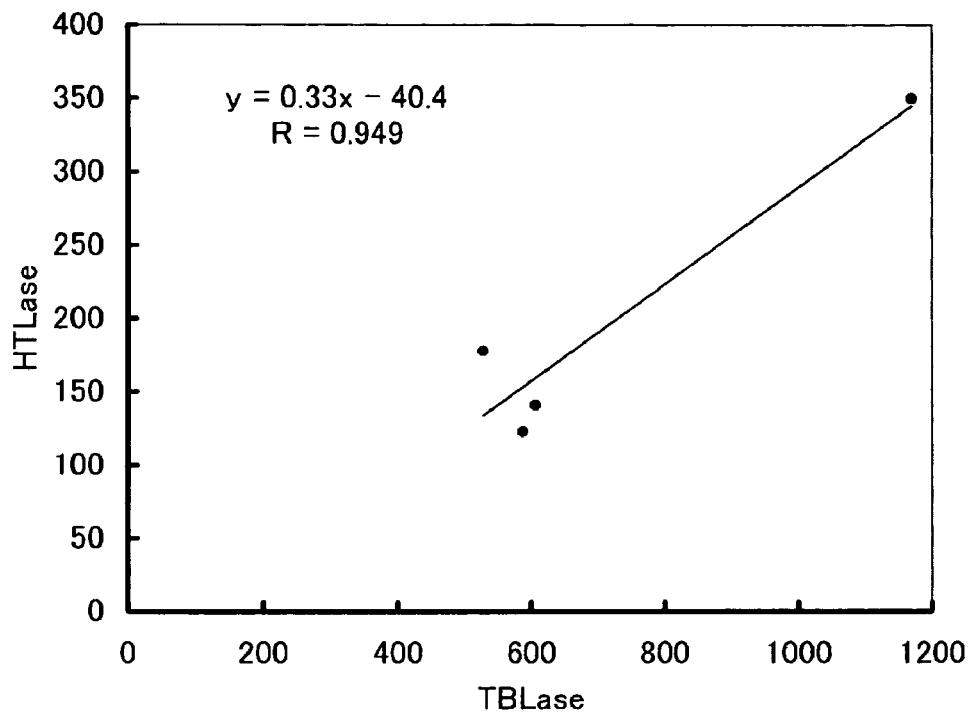
FIG. 5 illustrates the correlation between the HTL hydrolyzing enzyme activity in the presence of calcium and the TBL hydrolyzing enzyme activity in the absence of a cholinesterase inhibitor.

FIG. 5 shows the correlation between the results (Y) of measurement of the hydrolyzing enzyme activity for HTL in the presence of calcium (indicated as HTLase in the figure) and the results (X) of measurement of the hydrolyzing activity for TBL in the absence of a cholinesterase inhibitor (indicated as TBLase in the figure). The regression line is of the equation Y=0.33X−40.4, and the correlation coefficient R=0.949.

Figure 6:
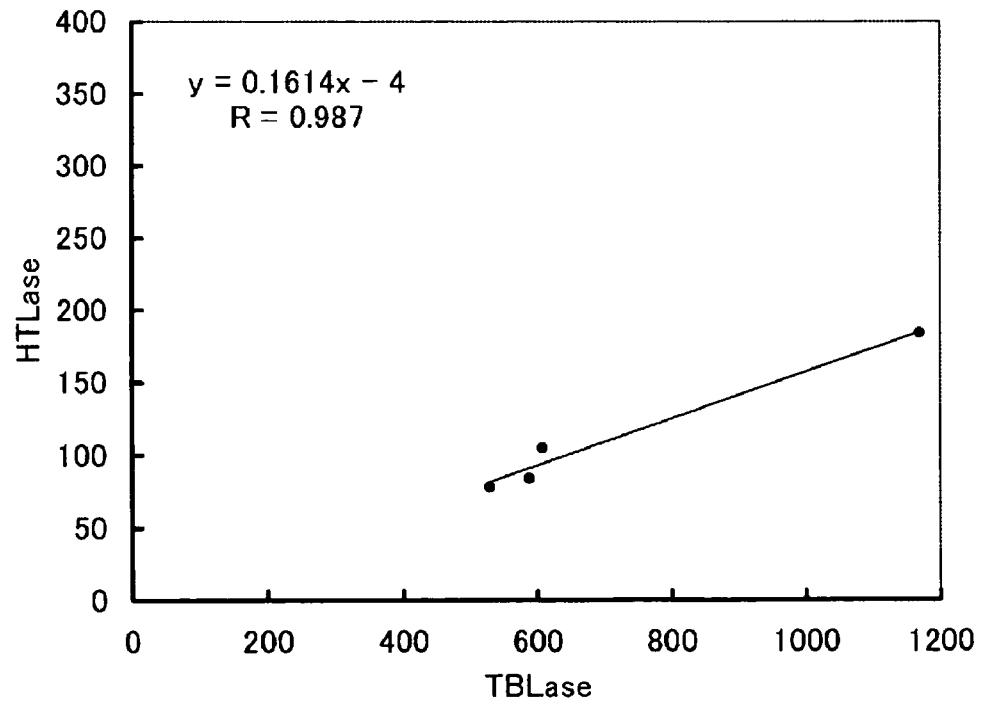
FIG. 6 illustrates the correlation between the calcium-dependent part of activity of the HTL hydrolyzing enzyme activity and the TBL hydrolyzing enzyme activity in the absence of a cholinesterase inhibitor.

FIG. 6 shows the correlation between the calcium dependent part of activity (Y) of the HTL hydrolyzing enzyme activity (which is the potion of the activity enhanced by calcium ion, i.e., the portion corresponding to the net HTL hydrolyzing activity of interest) and the results (X) of measurement of the TBL hydrolyzing enzyme activity in the absence of a cholinesterase inhibitor. The regression line is of the equation Y=0.161X−4, and the correlation coefficient R=0.987.

Figure 7:
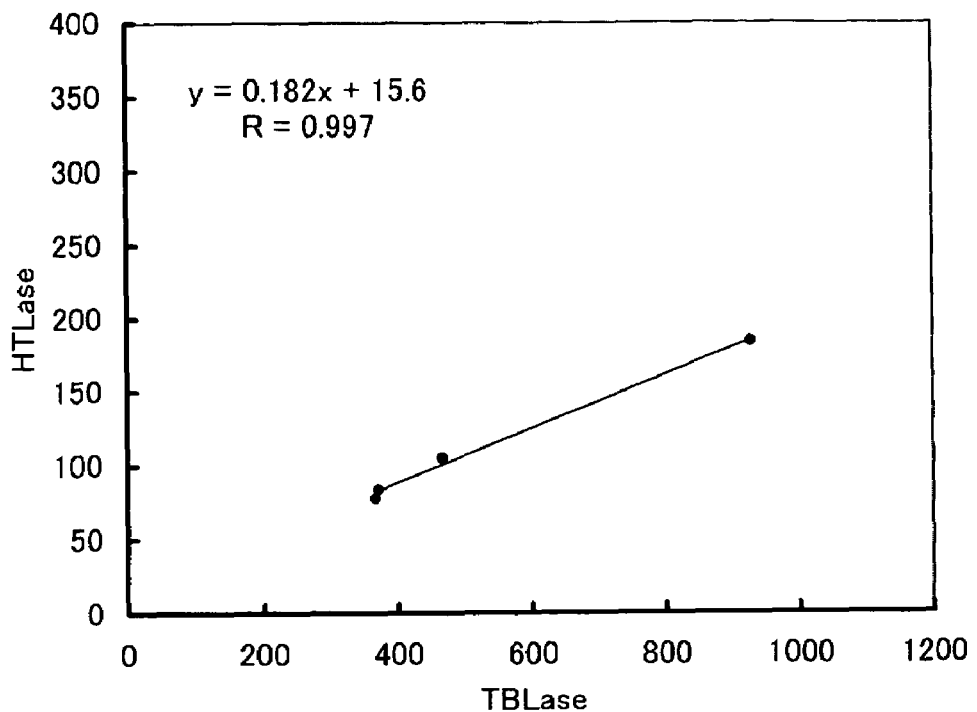
FIG. 7 illustrates the correlation between the calcium-dependent part of activity of the HTL hydrolyzing enzyme activity and the calcium-dependent part of activity of the TBL hydrolyzing enzyme activity.

FIG. 7 shows the correlation between the calcium dependent part of activity (Y) of the HTL hydrolyzing enzyme activity and the calcium dependent part of activity (X) of the TBL hydrolyzing enzyme activity. The regression line is of the equation Y=0.182X+15.6, and the correlation coefficient R=0.997.

Figure 8:
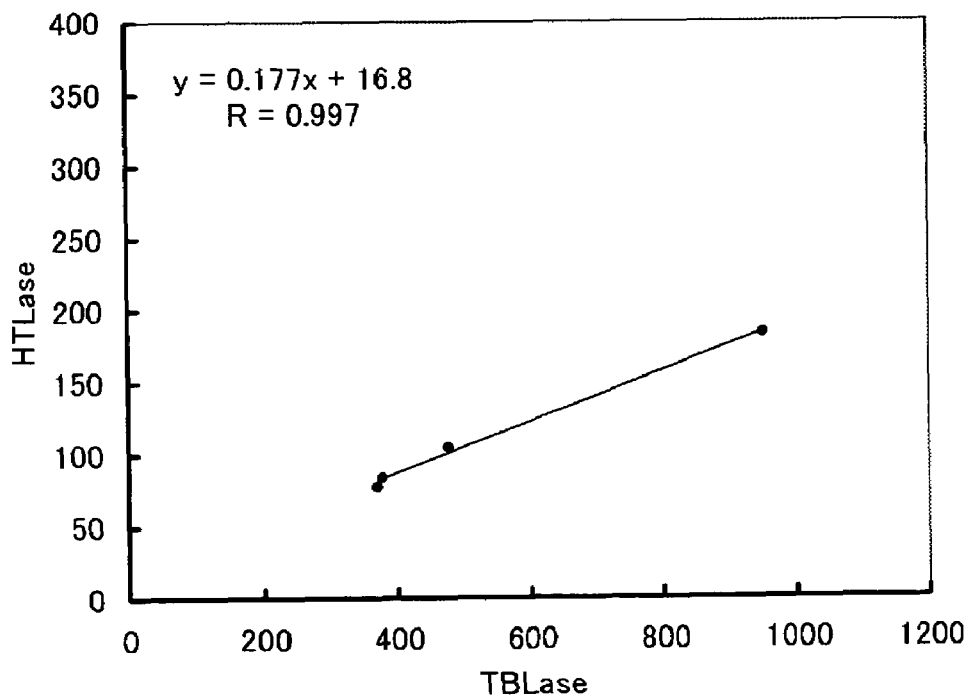
FIG. 8 illustrates the correlation between the calcium-dependent part of activity of the HTL hydrolyzing enzyme activity and the TBL hydrolyzing enzyme activity in the presence of a cholinesterase inhibitor (the method of the present invention).

FIG. 8 shows the correlation between the calcium dependent part of activity (Y) of the HTL hydrolyzing enzyme activity and the results of measurement of TBL hydrolyzing enzyme activity (X) in the presence of a cholinesterase inhibitor. The regression line is of the equation Y=0.177X+16.8, and the correlation coefficient R=0.997.

Thus, the correlation (FIG. 8) between the TBL hydrolyzing enzyme activity in the presence of a cholinesterase inhibitor and the calcium dependent part of activity of the HTL hydrolyzing enzyme activity is equivalent to the correlation (FIG. 7) between the calcium dependent part of activity of the TBL hydrolyzing enzyme activity and the calcium dependent part of activity of the HTL hydrolyzing enzyme activity. Therefore, TBL hydrolyzing enzyme activity in the presence of a cholinesterase inhibitor strongly reflects the net HTL hydrolyzing enzyme activity.

INDUSTRIAL APPLICABILITY

The method of the present invention for measurement of the activity of the HTL hydrolyzing enzyme can be used as a safe, quick and convenient method for measurement in daily testing, for it makes it possible to measure the activity of the HTL hydrolyzing enzyme in a sample without employing a radio-labeled substrate. In addition, the method of the present invention for measurement of the activity of the HTL hydrolyzing enzyme allows diagnosis and prognosis of relating diseases to be done within a short time, for it has such advantages over conventional methods that it can shorten the time required for measurement and is applicable to automatic analyzers, and thus enables more accurate and quicker measurement as compared with conventional methods. Therefore, the present invention provides a highly useful method for measurement of the activity of the HTL hydrolyzing enzyme.

I claim:

1. A method for measurement of the activity of a homocysteinethiolactone hydrolyzing enzyme in a sample, comprising mixing and reacting γ-thiobutyrolactone and the sample in the presence of a cholinesterase inhibitor;

detecting 4-mercaptobutyric acid thereby produced in a time window; and calculating the amount of 4-mercaptobutyric acid produced per unit of time to calculate a rate, correlating the rate with the activity of homocysteinethiolactone hydrolyzing enyme.

2. The method of claim 1, wherein the reaction is conducted in the presence of a divalent cation.

3. The method of claim 2, wherein the divalent cation is $Ca^{2+}$, $Ni^{2+}$ or $Fe^{2+}$.

4. The method of claim 2, wherein the concentration of the divalent cation is 0.1-10 mM.

5. The method of claim 1, wherein the cholinesterase inhibitor is physostigmine or a salt thereof, neostigmine or a salt thereof, or 4-bromobenzeneboronic acid or a salt thereof.

6. The method of claim 5, wherein the concentration of physostigmine or a salt thereof is 10 μM to 10 mM, the concentration of neostigmine or a salt thereof is 10 μM to 10 mM and the concentration of 4-bromobenzeneboronic acid or a salt thereof is 10 μM to 1 mM.

7. The method of claim 1, wherein the product 4-mercaptobutyric acid is detected using a thiol group detection reagent.

8. The method of claim 7, wherein the thiol group detection reagent is 5,5'-dithiobis(2-nitrobenzoic acid), 4,4'-bis(dimethylamino)benzhidrol, 2,2'-dithiodipyridine, 4,4'-dithiodipyridine, 2,2'-dithiobis(5-nitropyridine) or 6 6'-dithiobisnicotinic acid.

9. A reagent for measurement of the activity of homocysteinethiolactone hydrolyzing enzyme comprising γ-thiobutyrolactone and a cholinesterase inhibitor.

10. The reagent of claim 9 further comprising a thiol group detection reagent.

11. A kit for measurement of the activity of homocysteinethiolactone hydrolyzing enzyme, which comprises containers separately containing γ-thiobutyrolactone and a cholinesterase inhibitor, and which optionally comprises an additional container separately containing a thiol group detection reagent.

12. A kit for measurement of the activity of homocysteinethiolactone hydrolyzing enzyme, which comprises multiple containers or one container having multiple separated zones, containing a mixture consisting of γ-thiobutyrolactone and a cholinesterase inhibitor and optionally a thiol group detection reagent.

13. A kit for measurement of the activity of homocysteinethiolactone hydrolyzing enzyme, which comprises strips impregnated with γ-thiobutyrolactone and a cholinesterase inhibitor and optionally with a thiol group detection reagent.

* * * * *